(12) United States Patent
Takahashi et al.

(10) Patent No.: US 9,382,560 B2
(45) Date of Patent: Jul. 5, 2016

(54) METHOD FOR PRODUCING AMIDE COMPOUND

(71) Applicant: MITSUBISHI RAYON CO., LTD., Chiyoda-ku (JP)

(72) Inventors: Michiko Takahashi, Kanagawa (JP); Makoto Kano, Kanagawa (JP); Kozo Murao, Kanagawa (JP)

(73) Assignee: MITSUBISHI RAYON CO., LTD., Chiyoda-ku (JP)

( * ) Notice: Subject to any disclaimer, the term of this patent is extended or adjusted under 35 U.S.C. 154(b) by 0 days.

(21) Appl. No.: 14/648,532

(22) PCT Filed: Feb. 12, 2014

(86) PCT No.: PCT/JP2014/000718
§ 371 (c)(1),
(2) Date: May 29, 2015

(87) PCT Pub. No.: WO2014/129144
PCT Pub. Date: Aug. 28, 2014

(65) Prior Publication Data
US 2015/0315619 A1    Nov. 5, 2015

(30) Foreign Application Priority Data
Feb. 19, 2013    (JP) ................................ 2013-030188

(51) Int. Cl.
*C07C 233/09*    (2006.01)
*C12P 13/02*    (2006.01)
*C08F 20/56*    (2006.01)

(52) U.S. Cl.
CPC ............... *C12P 13/02* (2013.01); *C07C 233/09* (2013.01); *C08F 20/56* (2013.01)

(58) Field of Classification Search
CPC ........ C07C 233/09; C12P 13/02; C08F 20/56
See application file for complete search history.

(56) References Cited

U.S. PATENT DOCUMENTS

| 6,043,061 | A  |   | 3/2000 | Ishii et al. |
| 2009/0171051 | A1 | * | 7/2009 | Shibamoto ............ C07C 231/06 526/303.1 |
| 2011/0008853 | A1 | * | 1/2011 | Armitage ................ C12P 13/02 435/129 |

FOREIGN PATENT DOCUMENTS

| JP | 11-123098 |   | 5/1999 |
| JP | 2001-288156 | A | 10/2001 |
| JP | 2005-295815 | A | 10/2005 |
| JP | 2010-172295 | A | 8/2010 |
| JP | 2012-31126 | A | 2/2012 |
| JP | 2012-62268 | A | 3/2012 |
| WO | 2007/043466 | A1 | 4/2007 |

OTHER PUBLICATIONS

International Search Report issued May 20, 2014 in PCT/JP2014/000718 filed Feb. 12, 2014.

* cited by examiner

*Primary Examiner* — Shailendra Kumar
(74) *Attorney, Agent, or Firm* — Oblon, McClelland, Maier & Neustadt, L.L.P.

(57) ABSTRACT

The invention pertains to a technique for suppressing a decrease in nitrile hydratase activity and improving the productivity of the amide compound in the course of producing an amide compound from a nitrile compound using a biocatalyst. Specifically, the invention pertains to a method for producing the corresponding amide compound from a nitrile compound in the presence of a biocatalyst having nitrile hydratase activity, wherein the method for producing an amide compound using a nitrile compound is characterized in that the zinc concentration of the nitrile compound is 0.4 ppm or less.

15 Claims, No Drawings

METHOD FOR PRODUCING AMIDE COMPOUND

This application is a 371 of PCT/JP14/00718, filed on Feb. 12, 2014.

FIELD OF THE INVENTION

The present invention relates to a method for producing an amide compound, more specifically, a method for producing a corresponding amide compound from a nitrile compound by using a biocatalyst.

BACKGROUND ART

Amide compounds are extensively used as important materials in industrial fields. Acrylamides are widely used in coagulants for wastewater treatment, paper reinforcing agents, oil recovery agents and the like, whereas methacrylamides are used in coating materials, adhesives and so on.

In conventional industrial production methods, reduced copper as a catalyst was used to catalyze the hydration of nitrile compounds to produce their corresponding amide compounds. In recent years, nitrile hydratases with nitrile hydration activity capable of hydrating nitrile groups to convert them into amide groups were found among the enzymes found in microorganisms, and nitrile hydratase enzymes or microbial cells containing the enzymes are used to produce amide compounds from nitrile compounds. Compared with conventional methods that use metal catalysts, such production methods are characterized by milder reaction conditions, higher conversion rates from nitrile compounds to their corresponding amide compounds, and higher selectivity. Such methods are excellent from an industrial viewpoint and make it easier to design simpler production procedures.

When amide compounds are industrially produced by using nitrile hydratases, it is important that nitrile compounds are capable of efficiently producing their corresponding amide compounds. Accordingly, methods have been proposed such as enhancing nitrile hydratase enzyme activity (patent publication 1), preventing a decrease in nitrile hydratase activity caused by high temperatures, and enhancing their tolerance to amide compounds (patent publication 2). Other proposed methods are identifying organic impurities which adversely affect the enzyme activity in nitrile compounds so as to prevent lowered activity (patent publications 3~5): for example, reducing the benzene concentration in nitrile compounds (patent publication 3); and reducing the hydrocyanic acid concentration in nitrile compounds (patent publications 4, 5).

PRIOR ART PUBLICATION

Patent Publication

Patent publication 1: JP2005-295815A
Patent publication 2: JP2010-172295A
Patent publication 3: WO2007/043466
Patent publication 4: JP H11-123098A
Patent publication 5: JP2001-288156A

SUMMARY OF THE INVENTION

Problems to be Solved by the Invention

During the course of studies for enhancing productivity of amide compounds using enzymes, the inventors of the present invention have observed enzyme deactivation, which cannot be explained by the impurities in nitrile compounds disclosed in aforementioned patent publications. Accordingly, in a process for producing amide compounds from nitrile compounds by using biocatalysts, the present invention proposes a method for analyzing and removing materials that cause enzyme deactivation so that the lowering of nitrile hydratase activity is prevented and the productivity of amide compounds is improved.

Solutions to the Problems

The inventors of the present invention have studied to solve the above-described problems and found that when amide compounds are produced from nitrile compounds by using biocatalysts, amide compounds are efficiently produced by reducing the zinc concentration in nitrile compounds.

Namely, the present invention is characterized by the following [1]~[15].

[1] A method for producing a corresponding amide compound from a nitrile compound in the presence of a biocatalyst having nitrile hydratase activity, in which the zinc concentration in the nitrile compound is set at 0.4 ppm or lower, preferably 0.3 ppm or lower, more preferably 0.2 ppm or lower.

[2] The method for producing an amide compound described in [1], in which the zinc concentration in a nitrile compound is 0.1 ppm or lower.

[3] The method for producing an amide compound described in [1] or [2], in which the hydrocyanic acid concentration in a nitrile compound is set at 1.5 ppm or lower, preferably 1.0 ppm or lower, more preferably 0.8 ppm or lower.

[4] The method for producing an amide compound described in [3], in which the hydrocyanic acid concentration in a nitrile compound is set at 0.5 ppm or lower.

[5] The method for producing an amide compound described in any of [1]~[4], in which a nitrile compound is subjected to a purification process to reduce zinc, hydrocyanic acid and other impurities.

[6] The method for producing an amide compound described in [5], in which the purification process includes one or multiple procedures selected from among distillation, alkali treatment, ion exchange resin and removal by adsorption (removal using adsorbents such as activated carbon, activated alumina, zeolite and silica gel).

[7] The method for producing an amide compound described in any of [1]~[6], in which a nitrile compound is acrylonitrile and the amide compound is acrylamide.

[8] The method for producing an amide compound described in any of [1]~[7], in which a biocatalyst having nitrile hydratase activity is selected from animal cells, plant cells, organelles, microbial cells, or their treated products, that have nitrile hydratase activity.

[9] The method for producing an amide compound described in [8], in which the microorganisms having nitrile hydratase activity are *Rhodococcus* bacteria or *E. coli*.

[10] The method for producing an amide compound described in [8] or [9], in which a biocatalyst having nitrile hydratase activity is selected from bacterial cells capable of expressing nitrile hydratase derived from *Rhodococcus* bacteria or *Pseudonocardia* bacteria.

[11] The method for producing an amide compound described in any of [1]~[10], in which a biocatalyst having nitrile hydratase activity is contained at 4~20 mass %, preferably 5~15 mass %, more preferably 5~10 mass %, even more preferably 8 mass %, in terms of dry cells.

[12] An acrylamide solution produced in the method described in any of [1]~[11], in which the zinc concentration is set at 0.4 ppm or lower, preferably 0.3 ppm or lower, more preferably 0.2 ppm or lower.

[13] The acrylamide solution described in [12], in which the zinc concentration is set at 0.1 ppm or lower.

[14] The acrylamide solution described in [12] or [13], in which the hydrocyanic acid concentration is set at 1.5 ppm or lower, preferably 0.8 ppm or lower.

[15] The acrylamide solution described in [12] or [13], in which the hydrocyanic acid concentration is set at 0.5 ppm or lower.

Effects of the Invention

According to the embodiments of the present invention, a decrease in nitrile hydratase activity is suppressed so that nitrile compounds efficiently produce their corresponding amide compounds.

The present application is based upon and claims the benefit of priority to Japanese Patent Application No. 2013-030188. The entire contents of the application are incorporated herein by reference.

DETAILED DESCRIPTION OF THE EMBODIMENTS

The embodiments of the present invention are described in the following. (Biocatalyst having nitrile hydratase activity)

In the embodiments of the present invention, a nitrile hydratase indicates an enzyme capable of hydrating a nitrile compound and producing a corresponding amide compound. Such a biocatalyst having nitrile hydratase activity may be nitrile hydratase protein itself, or it may be animal cells, plant cells, organelles, bacterial cells or their treated products.

Examples of treated products are those obtained by crushing animal cells, plant cells, organelles or bacterial cells; enzymes extracted from bacterial cells (raw enzymes or purified enzymes); and those obtained by immobilizing animal cells, plant cells, organelles, bacterial cells or enzymes themselves on a carrier.

A comprehensive method, cross-linking method, carrier-binding method or the like may be used as an immobilizing method. A comprehensive method is to coat cells or the like with a polymer membrane; a crosslinking method is to crosslink enzymes using an agent having two or more functional groups (polyfunctional crosslinking agent); and a carrier-binding method is to bind enzymes to a water-insoluble carrier.

As for a single substance to be used for immobilization (immobilization carrier), examples are glass beads, silica gels, polyurethanes, polyacrylamides, polyvinyl alcohols, carrageenans, alginic acids, agars and gelatins.

Examples to represent such microorganisms are those having nitrile hydratase activity such as the genus *Rhodococcus*, genus *Gordona*, genus *Pseudomonas*, genus *Pseudonocardia*, genus *Geobacillus*, genus *Bacillus*, genus *Bacteridium*, genus *Micrococcus*, genus *Brevibacterium*, genus *Corynebacterium*, genus *Nocardia*, genus *Microbacterium*, genus *Fusarium*, genus *Agrobacterium*, genus *Acinetobacter*, genus *Xanthobacter*, genus *Streptomyces*, genus *Rhizobium*, genus *Klebsiella*, genus *Enterobacter*, genus *Erwinia*, genus *Pantoea*, genus *Candida*, genus *Aeromonas*, genus *Citrobacter*, and genus *Achromobacter*.

Specific examples are *Nocardia* sp. N-775 described in JP S56-17918B; *Rhodococcus rhodochrous* J1 described in JP H06-55148B; *Rhodococcus rhodochrous* strain NCIMB 41164 described in WO2005/054456; *Klebsiella* sp. MCI 2609 described in JP H05-30982A; *Aeromonas* sp. MCI 2614 described in JP H05-30983A; *Citrobacter freundii* MCI 2615 described in JP H05-30984A; *Agrobacterium rhizogenes* IAM 13570 and *Agrobacterium tumefaciens* described in JP H05-103681A; *Xanthobacter flavus* JCM 1204 and *Erwinia nigrifluens* MAFF 03-01435 described in JP H05-161495A; *Enterobacter* sp. MCI 2707 described in JP H05-236975A; *Streptomyces* sp. MCI 2691 described in JP H05-236976; *Rhizobium* sp. MCI 2610, *Rhizobium* sp. MCI 2643, *Rhizobium loti* IAM 13588, *Rhizobium leguminosarum* IAM 12609 and *Rhizobium merioti* IAM 12611 described in JP H05-236977A; *Candida guilliermondii* NH-2, *Pantoea agglomerans* NH-3, and *Klebsiella pneumoniae* NH-26T2 described in JP H05-15384A; *Agrobacterium radiobacter* SC-C15-1 described in JP H06-14786A; *Bacillus smithii* SC-J05-1 described in JP H07-25494A; *Pseudonocardia thermophila* ATCC19285 described in JP H08-56684A; and *Pseudonocardia thermophila* JCM3095 described in JP H09-275978A.

*Rhodococcus rhodochrous* J1 described in JP H06-551488 was deposited as accession number "FERM BP-1478" on Sep. 18, 1987, in National Institute of Technology and Evaluation Patent Organism Depositary Center (Chuo 6, 1-1-1 Higashi, Tsukuba-shi, Ibaraki Prefecture, Japan (the same reference information applies in the present application).

*Rhodococcus rhodochrous* NCIMB41164 described in WO2005/054456 was deposited as accession number "NCIMB41164" on Mar. 5, 2003 in National Collection of Industrial, Food and Marine Bacteria, Ltd. (NCIMB) (NCIMB Ltd Ferguson Building, Craibstone Estate, Bucksburn, Aberdeen AB21 9YA).

*Pseudonocardia thermophila* strain JCM3095 described in JP H09-275978A was deposited as accession number "FERM BP-5785" on Feb. 7, 1996 in National Institute of Technology and Evaluation Patent Organism Depositary Center (Chuo 6, 1-1-1 Higashi, Tsukuba-shi, Ibaraki Prefecture, Japan.)

In the embodiments of the present invention, one single microorganism or a combination of two or more may be used by selecting from those listed above.

The gene encoding a nitrile hydratase may be introduced or expressed in microbial cells by conventional molecular biology techniques (for such molecular biology techniques, refer to the following: Sambrook, Fritsch and Maniatis, "Molecular Cloning: A Laboratory Manual" 2nd Edition (1989), Cold Spring Harbor Laboratory Press). Namely, the embodiments of the present invention may employ enzymes obtained by introducing nucleic acids encoding natural nitrile hydratases (wild type) or their mutants (modified type) into microbial cells. Also, such enzymes may be used alone or in a combination thereof in the embodiments.

Each amino-acid sequence of wild-type nitrile hydratases is published in NCBI databases such as GenBank (http://www.ncbi.nlm.nih.gov/).

For example, the accession number of the α subunit derived from *Rhodococcus rhodochrous* J1 (FERM BP-1478) is "P21219," and the accession number of the β subunit is "P21220." In addition, the accession number of the α subunit derived from *Rhodococcus rhodochrous* strain M8 (SU 1731814) is "ATT 79340," and the accession number of the β subunit is "AAT 79339." Moreover, the accession number of the α subunit derived from *Pseudomonas thermophila* strain JCM3095 is "1 IRE A," and the accession number of the β subunit is "1 IRE B."

Examples of a transformant into which the gene of a wild-type nitrile hydratase was introduced are *E. coli* MT10770 (FERM P-14756) transformed with the nitrile hydratase gene of the genus *Achromobacter* (JP H08-266277A); *E. coli* MT10822 (FERM BP-5785) transformed with the nitrile hydratase gene of the genus *Pseudonocardia* (JP H09-275978A); and microorganisms transformed with the nitrile hydratase gene of the genus *Rhodococcus rhodochrous* (JP H04-211379A). However, they are not the only options.

Also known are modified types (mutants) obtained by substituting amino acids in wild-type nitrile hydratases (for example, those described in JP2010-172295A, JP2007-143409A and JP2007-043910A). Microorganisms into which such modified nitrile hydratases are introduced may also be used in the methods of the embodiments.

Microorganisms or their treated products having nitrile hydratase activity may be used for reactions to synthesize amide compounds immediately after bacterial cells are prepared, or they may be stored after being prepared and then used for amide synthesis reactions. Methods for cultivating microorganisms to prepare bacterial cells may be selected according to the types of microorganisms. Preculture may be performed prior to main culture.

Microbial cells or their treated products having nitrile hydratase activity may be used for batch reactions or continuous reactions. Methods using fluidized beds, fixed beds and suspended beds may be employed. The temperature of a biocatalyst in the reaction liquid is not limited specifically, as long as it does not cause difficulty in mixing the water-soluble medium and nitrile compound.

The water-soluble medium above indicates water, a buffer such as phosphates, or a solution (the entire reaction liquid) obtained by dissolving an appropriate concentration of inorganic salt such as sulfates or carbonates, alkali metal hydroxides, amide compounds, nitrile compounds, catalysts having nitrile hydratase activity and the like.

In the production method related to the present invention, reaction temperature (temperature of reaction mixture) is not limited specifically, but it is preferred to be 10~40° C., more preferably 20~35° C. If the reaction temperature is 10° C. or higher, the reaction activity of a biocatalyst is sufficiently enhanced while the temperature of cooling water can be set higher than otherwise. Thus, a cooling tower may be used instead of a freezer, and the energy for cooling water is lowered. In addition, if the reaction temperature is 40° C. or lower, deactivation of microbial catalysts is easier to suppress.

Reaction time in the production method according to the embodiments of the present invention is not limited specifically, but it is preferred to be 1~50 hours, for example, more preferably 3~20 hours.

When resting microbial cells that have been isolated from the culture liquid and washed are used for producing compounds, the concentration of dry cells of the resting microbial cells to be suspended is preferred to be 4 mass % or greater, more preferably 5 mass % or greater, in terms of dry cells. However, if the cell concentration exceeds 20 mass %, the fluidity of a cell suspension is lowered, making it harder to handle the liquid. Thus, the concentration of a cell suspension is preferred to be 4~20 mass %, more preferably 5~15 mass %, even more preferably 5~10 mass %, especially preferably 8 mass %, in terms of dry cells.

(Nitrile Compound)

Regarding a nitrile compound used as a raw material in a production method related to the present invention, it is not limited specifically as long as it is capable of being converted into an amide compound by a catalyst having a nitrile hydratase activity. Examples are aliphatic saturated nitriles such as such as acetonitrile, propionitrile, succinonitrile and adiponitrile; aliphatic unsaturated nitriles such as acrylonitrile and methacrylonitrile; aromatic nitriles such as benzonitrile and phthalodinitrile; and heterocyclic nitriles such as nicotinonitrile. Nitrile compounds in the present embodiment are preferred to be those having 2~4 carbon atoms, for example, acetonitrile, propionitrile, acrylonitrile, methacrylonitrile, n-butyronitrile, isobutyronitrile and the like. Especially preferred are acrylonitrile, methacrylonitrile and acetonitrile.

(Reducing Hydrocyanic Acid in Nitrile Compound)

Nitrile compounds such as those listed above are purified and set as commercially available products. For example, acrylonitrile is industrially produced by ammoxidation of propylene, and hydrocyanic acid is removed along with other byproducts by purifying the reaction mixture through distillation after the reaction is completed. Hydrocyanic acid that was not removed in the process is contained in a commercially available product. In the production method according to the present embodiment, the amount of hydrocyanic acid in the nitrile compound as raw material is preferred to be lowered.

The hydrocyanic acid remaining in the nitrile compound used in the present embodiment is further reduced through chemical methods. Preferred methods are those that will neither cause nitrile compounds to degenerate nor increase byproducts and impurities that may decrease the quality of amide compounds to be produced, for example, a method using ion exchange resin, a method for adding hydrocyanic acid to a nitrile compound under alkaline conditions when the nitrile compound is unsaturated nitrile (see patent publications 4, 5), and the like.

The amount of hydrocyanic acid to be removed is preferred to be greater. Usually, the amount is reduced so that the hydrocyanic acid concentration in a nitrile compound is 1.5 ppm or lower, preferably 0.8 ppm or lower, more preferably 0.5 ppm or lower. The hydrocyanic acid concentration may also be at or below the detection limit.

The hydrocyanic acid concentration in an acrylonitrile compound is determined by titration using silver nitrate after the hydrocyanic acid is extracted by an alkaline solution. Alternatively, the concentration is determined by spectrophotometry.

(Reducing Zinc in Nitrile Compound)

One of the impurities found at trace amounts in nitrile compounds is zinc. For example, commercially available acrylonitrile, which is industrially produced by ammoxidation of propylene, contains zinc derived from a trace amount of zinc contained in the production line or the like.

The zinc concentration in a nitrile compound used in the present embodiment may be selected at any level as long as it does not cause a decrease in the reaction rate. The zinc concentration in a nitrile compound is usually preferred to be 0.4 ppm or lower, more preferably 0.3 ppm or lower, even more preferably 0.2 ppm or lower, especially preferred to be 0.1 ppm or lower. Any available method may be used to remove zinc from a nitrile compound, for example, distillation methods, adsorption removal methods using activated carbon, activated alumina, zeolite, silica gel or the like, and methods using anion exchange resin and the like.

In addition, the zinc concentration in acrylonitrile can be measured by inductively coupled plasma spectrometry.

By reducing the zinc concentration in a nitrile compound as described above, a decrease in nitrile hydratase activity is suppressed and the reaction rate in synthesizing the amide compound is enhanced. The effects of zinc reduction are further enhanced by removing/reducing other organic impurities contained in the nitrile compound (such as benzene, hydrocyanic acid, acrolein, oxazole).

Removal of zinc and other impurities as mentioned above can be achieved by using well-known purification procedures in the art, for example, by employing the above-listed methods such as distillation, alkali treatment, removal by adsorption, anion exchange resin and the like.

(High-Quality Acrylamide Solution)

The amide compound obtained by the method according to the present embodiment, especially solutions containing acrylamide, is a high-quality acrylamide compound with reduced concentrations of zinc and organic impurities such as hydrocyanic acid.

The zinc concentration in the acrylamide solution related to the present invention is 0.4 ppm or lower, preferably 0.3 ppm or lower, more preferably 0.2 ppm or lower, most preferably 0.1 ppm or lower. In addition, its hydrocyanic acid concentration is 1.5 ppm or lower, preferably 0.8 ppm or lower, more preferably 0.5 ppm or lower. When the acrylamide solution related to the present embodiment is used, higher-quality acrylamide-based polymers are obtained.

EXAMPLES

In the following, examples of the present invention are described in further detail. However, the present invention is not limited to those. The percentages below indicate mass %.

Example 1

(Cell Preparation) *Rhodococcus rhodochrous* J1 (FERM BP-1478)

*Rhodococcus rhodochrous* J1 (FERM BP-1478) having nitrile hydratase activity was used. A culture medium (pH 7.0) was prepared by dissolving the following in tap water: glucose 2.0%, polypeptone 1.0%, monosodium glutamate 1%, potassium hydrogen phosphate 0.2%, dipotassium hydrogen phosphate 0.2%, magnesium sulfate heptahydrate 0.1% and cobalt chloride 0.01%. In the 3-liter mini jar fermenter (made by Takasugi Seisakusho), 2.5 liters of the prepared culture medium was placed and sterilized in an autoclave oven at 121° C. for 20 minutes. Then, 20 mL of *Rhodococcus rhodochrous* J1 was inoculated into the medium and cultivated in the dark at 35° C. and 230 rpm for 42 hours. Next, the culture was washed using 50 mM phosphate buffer (pH 7.0), and a cell suspension (3% in terms of dry cells) was obtained.

(Zinc Reduction Treatment of Acrylonitrile)

A fixed-bed type adsorbent of activated carbon containing 1 kg of activated carbon (inner surface area of 1000 $m^2$/kg) was placed in a reaction vessel, and acrylonitrile was passed through the vessel at a temperature of 10° C. After passing through the vessel, the acrylonitrile was recovered and its zinc concentration was measured by an inductively coupled plasma spectrometry device (ICAP577, made by Thermo Fisher Scientific, Inc.) It was found to be less than the lower detection limit of 0.07 ppm.

(Hydrocyanic Acid Reduction Treatment of Acrylonitrile)

In 10 liters of industrial acrylonitrile (containing hydrocyanic acid at 5 ppm), 50 grams of 0.1 M hydrogen sodium was added, stirred to be dissolved well, and let stand for 30 minutes to perform alkali treatment. Then, 10 grams of a 1 M acrylic acid solution was added to neutralize the acrylonitrile. After the treatment, it was found that the hydrocyanic acid concentration in the acrylonitrile was reduced to 0.5 ppm. The hydrocyanic acid concentration in acrylonitrile was measured by a spectrophotometer (DR500001, made by HACH Company) as follows.

(Method for Measuring Hydrocyanic Acid Concentration)

In a test tube, 9.6 grams of pure water and 0.4 grams of acrylonitrile were placed and let stand at 25° C. for 30 minutes. Next, CyaniVer.3 reagent in the HACH test kit was added and vortexed for 30 seconds and then let stand for 30 seconds. Then, after CyaniVer.4 reagent was added and vortexed for 10 seconds and CyaniVer.5 reagent was added and vortexed for 2 minutes, the test tube was let stand at 25° C. for 30 minutes. The concentration was measured by the spectrophotometer.

(Amide Producing Reaction)

In a plastic case with a lid (made by Shinsho Kizai) having an inner volume of 100 mL, 3.4 grams of a phosphate buffer, 93.1 grams of 50.5% acrylamide, and 3.0 grams of acrylonitrile were added and stirred while maintaining the temperature at 30° C. Then, 0.1 gram of the cells prepared above was added to initiate reactions. The reaction liquid was retrieved after 6 hours, and its acrylonitrile concentration was determined by gas chromatography (column: PoraPack-PS (made by Waters), 1 meter, 210° C.; carrier gas: helium; detector: FID). The acrylonitrile concentration prior to the reaction was set at 100%, and the reaction rate was calculated from the acrylonitrile concentration after the reaction. As a result, 82.7% of the acrylonitrile was found converted to acrylamide.

Example 2

Example 2 was conducted the same as Example 1 except that the time for the acrylonitrile to be in contact with hydrogen sodium was adjusted so that the hydrocyanic acid concentration in the acrylonitrile was set at 1.5 ppm. As a result, the reaction rate was 76.0%.

Example 3

Example 3 was conducted the same as Example 1 except that the hydrocyanic acid concentration in the acrylonitrile was set at 1.5 ppm, and the time to pass the acrylonitrile through the reaction vessel was adjusted to set the zinc concentration at 0.3 ppm. As a result, the reaction rate was 71.7%.

Example 4

Example 4 was conducted the same as Example 1 except that the hydrocyanic acid concentration in the acrylonitrile was set at 3.0 ppm and the zinc concentration at 0.3 ppm. As a result, the reaction rate was 42.3%.

Comparative Example 1

Comparative Example 1 was conducted the same as Example 1 except that the hydrocyanic acid concentration in the acrylonitrile was set at 0.5 ppm and the zinc concentration at 0.5 ppm. As a result, the reaction rate was 21.8%.

Comparative Example 2

Comparative Example 2 was conducted the same as Example 1 except that the hydrocyanic acid concentration in the acrylonitrile was set at 1.5 ppm and the zinc concentration at 0.5 ppm. As a result, the reaction rate was 18.5%.

Comparative Example 3

Comparative Example 3 was conducted the same as Example 1 except that the hydrocyanic acid concentration in the acrylonitrile was set at 2.0 ppm and the zinc concentration at 0.5 ppm. As a result, the reaction rate was 16.3%.

Example 5

(Cell Preparation) *Pseudonocardia thermophila* JCM 3095

As a transformant with a nitrile hydratase gene derived from *Pseudonocardia thermophila* JCM 3095, transformant *Rhodococcus rhodochrous* strain ATCC12674/psj-N02A, which was obtained by introducing plasmid psj-N02A described in JP2011-200132A into the strain ATCC12674 in the same manner described therein, was used in Example 5. Then, a culture medium (pH 7.0) was prepared by dissolving the following in tap water: glucose 15 g/L, yeast extract 1 g/L, monosodium glutamate 10 g/L, potassium hydrogen phosphate 0.5 g/L, dipotassium hydrogen phosphate 0.5 g/L, magnesium sulfate heptahydrate 0.5 g/L and cobalt chloride 1 g/L. In a 500-mL Erlenmeyer flask, 2.5 liters of the prepared medium was placed and sterilized in an autoclave oven at 121° C. for 20 minutes. Then, transformant ATCC12674/psj-N02A was inoculated into the medium and cultivated in the dark at 30° C. and 230 rpm for 72 hours.

(Hydrocyanic Acid Reduction Treatment of Acrylonitrile)
The same as in Example 1, the hydrocyanic acid concentration in the acrylonitrile was set at 0.5 ppm and the zinc concentration at the lower detection limit.

(Amide Producing Reaction)
The acrylamide concentration was set at 20% and the acrylonitrile concentration was set at 3% in 100 mL of the reaction liquid. By using a centrifuge, a catalyst was concentrated to be 10 times the concentration of the cultured cell liquid, and then 3.5 mL of the catalyst was added to the reaction liquid.

Example 5 was prepared the same as Example 1 except for the above procedures. When the reaction amount was measured five hours later, the decrease in acrylonitrile was 1.76%, which was 1.27 times that of Comparative Example 4.

Comparative Example 4

Comparative Example 4 was conducted the same as Example 5 except that the zinc concentration in the acrylonitrile was set at 0.5 ppm. When measured after 5 hours, the reaction amount of the acrylonitrile was found to be 1.38%.

Example 6

(Cell Preparation) *Rhodococcus rhodochrous* Strain NCIMB 41164

The nitrile hydratase derived from *Rhodococcus rhodochrous* strain NCIMB 41164 was prepared by the same method described in JP2007-512820. A culture medium was prepared with dipotassium hydrogen phosphate 0.7, potassium hydrogen phosphate 0.3, glucose 10.0, peptone 1.0, yeast extract 3.0, magnesium sulfate heptahydrate 0.5, urea 5.0, cobalt chloride hexahydrate 0.01 and tap water to make the entire amount 1 liter. In an Erlenmeyer flask with a 2 L baffle plate, 400 mL of the prepared culture medium was placed and the cells were grown. The pH of the medium was adjusted to 7.2 and the culture was grown at 28° C. for 5 days.

(Hydrocyanic Acid Reduction Treatment of Acrylonitrile)
The same as in Example 1, the hydrocyanic acid concentration in the acrylonitrile was set at 0.5 ppm and the zinc concentration at the lower detection limit.

(Amide Producing Reaction)
The acrylamide concentration was set at 20% and the acrylonitrile concentration was set at 3% in 100 mL of the reaction liquid. The cultured cell liquid was diluted to be 2.3 times the original by using a 50 mM phosphate buffer (pH 7.0) to prepare a catalyst. Then, 1.0 mL of the catalyst was added to the cell liquid. The rest was conducted the same as in Example 1. When the reaction amount was measured five hours later, the decrease in acrylonitrile was 2.13%, which was 2.47 times that of Comparative Example 5.

Comparative Example 5

Comparative Example 5 was conducted the same as Example 6 except that the zinc concentration in the acrylonitrile was set at 5.5 ppm. When measured after five hours, the decrease in acrylonitrile was 0.86%.

Table 1 below shows the results of examples and comparative examples.

TABLE 1

*Rhodococcus rhodochrous* J-1 (FERN BP-1478)

|  | hydrocyanic acid [ppm] | zinc [ppm] | reaction rate [%] |
|---|---|---|---|
| example 1 | 0.5 | <0.07 | 82.7 |
| example 2 | 1.5 | <0.07 | 76.0 |
| example 3 | 1.5 | 0.3 | 71.7 |
| example 4 | 3.0 | 0.3 | 42.3 |
| comp. example 1 | 0.5 | 0.5 | 21.8 |
| comp. example 2 | 1.5 | 0.5 | 18.5 |
| comp. example 3 | 2.0 | 0.5 | 16.3 |

From the examples above, when the hydrocyanic acid concentration is 1.5 ppm or lower and the zinc concentration is 0.4 ppm or lower, the reactivity is found to be high, with a reaction rate of 70% or greater. Especially, when the hydrocyanic acid concentration is 0.5 ppm and the zinc concentration is 0.1 ppm or lower in Example 1, the reactivity is even higher, with a high reaction rate of 80% or greater. Accordingly, when hydrocyanic acid and zinc are both reduced, it is found that the reaction rate further improves.

In addition, the results are shown in Tables 2 and 3 below when *Pseudonocardia thermophila* strain JCM 3095 and *Rhodococcus rhodochrous* strain NCIMB 41164 were used as catalysts respectively.

TABLE 2

*Pseudonocardia thermophila* strain JCM 3095

|  | hydrocyanic acid [ppm] | zinc [ppm] | reaction amount (AN concentration before reaction- AN concentration after reaction) [%] | relative reaction amount [—] |
|---|---|---|---|---|
| example 5 | 0.5 | <0.07 | 1.76 | 1.27 |
| comp. example 4 | 0.5 | 0.5 | 1.38 | 1.00 |

TABLE 3

| | Rhodococcus rhodochrous strain NCIMB 41164 | | | |
|---|---|---|---|---|
| | hydrocyanic acid [ppm] | zinc [ppm] | reaction amount (AN concentration before reaction- AN concentration after reaction) [%] | relative reaction amount [—] |
| example 6 | 0.5 | <0.07 | 2.13 | 2.47 |
| comp. example 5 | 0.5 | 5.5 | 0.86 | 1.00 |

From the results obtained in examples and comparative examples above, when the hydrocyanic acid concentration is 0.5 ppm, the reactivity is better at a zinc concentration of 0.1 ppm or less than at a zinc concentration of 5.5 ppm. Accordingly, setting those concentrations as above is found to be effective in microorganisms such as *Rhodococcus* bacteria and *Pseudonocardia* bacteria having nitrile hydratase activity.

INDUSTRIAL APPLICABILITY

According to the embodiments of the present invention, a decrease in nitrile hydratase enzyme activity is suppressed and amide compounds are efficiently produced.

All the publications, patents and patent applications cited in the present application are incorporated herein by reference.

What is claimed is:

1. A method for producing a corresponding amide compound from a nitrile compound in the presence of a biocatalyst having nitrile hydratase activity, in which zinc concentration in the nitrile compound is set at 0.4 ppm or lower.

2. The method for producing an amide compound according to claim 1, wherein the zinc concentration in the nitrile compound is 0.1 ppm or lower.

3. The method for producing an amide compound according to claim 1, wherein hydrocyanic acid concentration in the nitrile compound is set at 1.5 ppm or lower.

4. The method for producing an amide compound according to claim 3, wherein the hydrocyanic acid concentration in the nitrile compound is set at 0.5 ppm or lower.

5. The method for producing an amide compound according to claim 1, wherein the nitrile compound is subjected to a purification process.

6. The method for producing an amide compound according to claim 5, wherein the purification process includes one or multiple procedures selected from distillation, alkali treatment, ion exchange resin and removal by adsorption.

7. The method for producing an amide compound according to claim 1, wherein the nitrile compound is acrylonitrile and the amide compound is acrylamide.

8. The method for producing an amide compound according to claim 1, wherein the biocatalyst having nitrile hydratase activity is selected from animal cells, plant cells, organelles, microbial cells, and their treated products, which have nitrile hydratase activity.

9. The method for producing an amide compound according to claim 8, wherein the biocatalyst having nitrile hydratase activity is a *Rhodococcus* bacterium or *E. coli*.

10. The method for producing an amide compound according to claim 8, wherein biocatalysts having nitrile hydratase activity are bacterial cells capable of expressing nitrile hydratase derived from *Rhodococcus* bacteria or *Pseudonocardia* bacteria.

11. The method for producing an amide compound according to claim 1, wherein the biocatalyst having nitrile hydratase activity is contained at 4~20 mass % in terms of dry cells.

12. An acrylamide solution produced by the according to claim 1, wherein the zinc concentration is 0.4 ppm or lower.

13. The acrylamide solution according to claim 12, wherein the zinc concentration is 0.1 ppm or lower.

14. The acrylamide solution according to claim 12, wherein hydrocyanic acid concentration is 1.5 ppm or lower.

15. The acrylamide solution according to claim 12, wherein hydrocyanic acid concentration is 0.5 ppm or lower.

* * * * *